US011266528B2

(12) United States Patent
Barrett et al.

(10) Patent No.: US 11,266,528 B2
(45) Date of Patent: Mar. 8, 2022

(54) TREATMENT LASER WITH REFLEX MIRROR AND SAFETY INTERLOCK

(71) Applicant: ELLEX MEDICAL PTY LTD, Mawson Lakes (AU)

(72) Inventors: Bradley Barrett, Mawson Lakes (AU); David Haarhoff, Mawson Lakes (AU); Timothy Dixon, Mawson Lakes (AU)

(73) Assignee: ELLEX MEDICAL PTY LTD, Mawson Lakes (AU)

( * ) Notice: Subject to any disclaimer, the term of this patent is extended or adjusted under 35 U.S.C. 154(b) by 141 days.

(21) Appl. No.: 16/341,341

(22) PCT Filed: Sep. 18, 2017

(86) PCT No.: PCT/AU2017/051016
§ 371 (c)(1),
(2) Date: Apr. 11, 2019

(87) PCT Pub. No.: WO2018/068081
PCT Pub. Date: Apr. 19, 2018

(65) Prior Publication Data
US 2020/0046553 A1 Feb. 13, 2020

(30) Foreign Application Priority Data

Oct. 14, 2016 (AU) ................. 2016904178

(51) Int. Cl.
*A61F 9/008* (2006.01)
*A61B 90/00* (2016.01)
*A61B 18/20* (2006.01)

(52) U.S. Cl.
CPC .......... *A61F 9/008* (2013.01); *A61F 9/00825* (2013.01); *A61B 2018/20359* (2017.05);
(Continued)

(58) Field of Classification Search
CPC .................. A61F 9/008; A61F 9/00825; A61F 2009/00868; A61B 2090/049; A61B 2018/20359
See application file for complete search history.

(56) References Cited

U.S. PATENT DOCUMENTS 8,876,808 B2  11/2014  Feklistov et al.
9,060,846 B2   6/2015  Feklistov et al.
(Continued)

FOREIGN PATENT DOCUMENTS

EP   2384727 A1  11/2011
RU   2526423 C2   8/2014
(Continued)

OTHER PUBLICATIONS

WIPO Application No. PCT/AUZOI7/051016, PCT International Preliminary Report on Patentability dated Apr. 16, 2019.
(Continued)

*Primary Examiner* — Allen Porter
*Assistant Examiner* — Skylar Lindsey Christianson
(74) *Attorney, Agent, or Firm* — Alston & Bird LLP

(57) ABSTRACT

An ophthalmic laser system for generating a first beam at a first wavelength on a first beam path and a second beam at a second wavelength on a second beam path, and directing optics to selectively direct the first wavelength or the second wavelength to a treatment beam path. The ophthalmic laser system a reflex coaxial illuminator comprising a reflex mirror movable on an from a axis a position out of the treatment beam path to a position in the treatment beam path to direct illumination into an illumination path coaxial with the treatment beam path and a safety interlock only allowing operation of the ophthalmic laser system on the first beam path if the reflex coaxial illuminator is in a first position and allowing operation of the ophthalmic laser system on either (Continued)

the first beam path or the second beam path if the reflex coaxial illuminator is not in the first position.

17 Claims, 4 Drawing Sheets

(52) U.S. Cl.
CPC ............... *A61B 2090/049* (2016.02); *A61F 2009/00868* (2013.01); *A61F 2009/00887* (2013.01); *A61F 2009/00891* (2013.01)

(56) References Cited

U.S. PATENT DOCUMENTS

| | | | |
|---|---|---|---|
| 10,369,501 B2 | 8/2019 | Ralph | |
| 2002/0198516 A1* | 12/2002 | Knopp | A61F 9/00804 606/5 |
| 2004/0215175 A1* | 10/2004 | Feklistov | A61F 9/0084 606/4 |
| 2007/0093794 A1 | 4/2007 | Wang et al. | |
| 2015/0148786 A1* | 5/2015 | Plunkett | G02B 27/14 606/4 |
| 2015/0297408 A1 | 10/2015 | Dolzan et al. | |
| 2019/0209371 A1 | 7/2019 | Plunkett et al. | |
| 2019/0282403 A1 | 9/2019 | Barrett et al. | |

FOREIGN PATENT DOCUMENTS

| | | |
|---|---|---|
| WO | WO 2004/027487 A1 | 4/2004 |
| WO | WO 2006/021040 A2 | 3/2006 |
| WO | WO 2013/177611 A1 | 12/2013 |

OTHER PUBLICATIONS

WIPO Application No. PCT/AU2017/051016, PCT International Search Report dated Nov. 9, 2017.
WIPO Application No. PCT/AU2017/051016, PCT Written Opinion of the International Searching Authority dated Nov. 9, 2017.
RU 2019113520/14 Search Report dated Jan. 15, 2021.
JP 2019-518932 Notice of Reasons for Refusal dated Aug. 20, 2021.

* cited by examiner

TREATMENT LASER WITH REFLEX MIRROR AND SAFETY INTERLOCK

CROSS-REFERENCE TO RELATED APPLICATIONS

This application is the US national stage of PCT/AU2017/051016 filed Sep. 18, 2017, which claims the benefit of Australian Provisional Application No. 2016904178 filed Oct. 14, 2016.

FIELD OF THE INVENTION

The present invention relates to the field of ophthalmic lasers. More particularly, the invention relates to maintaining safety of users of ophthalmic laser systems.

BACKGROUND TO THE INVENTION

The Applicant has previously described an Ophthalmic Laser System that is useful for performing selective laser trabeculoplasty (SLT) and secondary cataract surgery procedures. The laser system is described in International Patent Application Number PCT/AU03/01224. The laser system generates a first beam at a wavelength suitable for performing secondary cataract surgery procedures (photodisruptor) and selectively generates a second beam at a wavelength suitable for treating glaucoma (SLT). Each beam may be selected using an extracavity deflection means to direct the beam down a selected beam path.

It is important in ophthalmic treatments for the ophthalmologist to be able to view the treatment zone for as long as possible during the treatment. For safety reasons the viewing path is blocked during the actual laser treatment to avoid the risk of damage to the eyes of the ophthalmologist due to reflection of the laser beam. The Applicant has developed a reflex coaxial illuminator that utilises a flip mirror that only intercepts the viewing path for the short period of the laser treatment. The invention is described in International Patent Application number PCT/AU2013/000546.

It would be desirable for all ophthalmic laser systems to be able to benefit from the reflex coaxial illuminator safety benefits. However, there are a number of problems to be addressed when looking to implement the reflex coaxial illuminator on the ophthalmic laser system described above. When operating in secondary cataract surgery mode the system must:
  illuminate the retina at the best possible angle (which is co-axial);
  allow the aiming beams to pass;
  allow the treatment beam to pass; and
  there should be no interference to the viewing path of the ophthalmologist.
When operating in SLT mode the system must:
  provide adequate illumination to the anterior of the eye;
  allow the aiming beam to pass;
  allow the treatment beam to pass; and
  there should be no interference to the viewing path of the ophthalmologist.

There is a need to find a solution that allows the SLT aiming beam to pass while providing adequate illumination.

SUMMARY OF THE INVENTION

In one form, although it need not be the only or indeed the broadest form, the invention resides in an ophthalmic laser system comprising:

a laser module producing a beam of short pulses of radiation with high energy density at a first wavelength;

a first beam path incorporating optical elements for directing the beam at the first wavelength into a treatment beam path to an eye of a patient;

a second beam path incorporating a frequency doubling module that converts the beam at the first wavelength to a beam at a second wavelength, and optical elements for directing the beam at the second wavelength to the treatment beam path;

beam steering optics for selectively deflecting the beam at the first wavelength into the second beam path, the beam steering optics being operable between a first position in which the beam at the first wavelength follows the first beam path and a second position in which the beam at the first wavelength is deflected to the second beam path;

a reflex coaxial illuminator comprising a reflex mirror movable on an axis from a position in the treatment beam path to a position out of the treatment beam path; and a safety interlock only allowing operation of the ophthalmic laser system on the first beam path if the reflex coaxial illuminator is in a first position and allowing operation of the ophthalmic laser system on either the first beam path or the second beam path if the reflex coaxial illuminator is not in the first position.

In another form the invention resides in an ophthalmic laser system for selective treatment of glaucoma and secondary cataract, the ophthalmic laser system comprising:

a laser module comprising a Q-switched laser which operates to produce pulsed radiation at a first wavelength;

a first beam path adapted to treating secondary cataract incorporating an attenuator, beam shaping optics, and directing optics for directing the beam of short pulses at the first wavelength along a treatment beam path to an eye of a patient with secondary cataract;

a second beam path adapted to treating glaucoma by selective laser trabeculoplasty incorporating a frequency conversion module that converts the pulsed beam at the first wavelength to a pulsed beam at a second wavelength; an attenuator, and directing optics for directing the pulsed beam at the second wavelength along the treatment beam path to an eye of a patient with glaucoma;

beam steering optics for selectively deflecting the beam of short pulses at the first wavelength into the second beam path, the beam steering optics being operable between a first position in which the pulsed beam at the first wavelength is received by and follows the first beam path and a second position in which the pulsed beam at the first wavelength is deflected to, received by and follows the second beam path;

a reflex coaxial illuminator comprising a reflex mirror movable on an axis from a position out of the treatment beam path to a position in the treatment beam path, wherein the reflex mirror directs illumination into an illumination path coaxial with the treatment beam path; and a safety interlock only allowing operation of the ophthalmic laser system on the first beam path if the reflex coaxial illuminator is in a first position and allowing operation of the ophthalmic laser system on either the first beam path or the second beam path if the reflex coaxial illuminator is not in the first position.

In a still further form the invention resides in a method of treating secondary cataracts or glaucoma using the ophthalmic laser system including the steps of:

operating the beam steering optics to select the first or second beam path depending on whether the patient has secondary cataract or glaucoma;

operating the safety interlock for either operation only on the first beam path or operation on either the first beam path or the second beam path; and operating the laser system through the selected beam path to treat the patient.

Further features and advantages of the present invention will become apparent from the following detailed description.

BRIEF DESCRIPTION OF THE DRAWINGS

To assist in understanding the invention and to enable a person skilled in the art to put the invention into practical effect, preferred embodiments of the invention will be described by way of example only with reference to the accompanying drawings, in which.

DETAILED DESCRIPTION OF THE INVENTION

Figure 1:
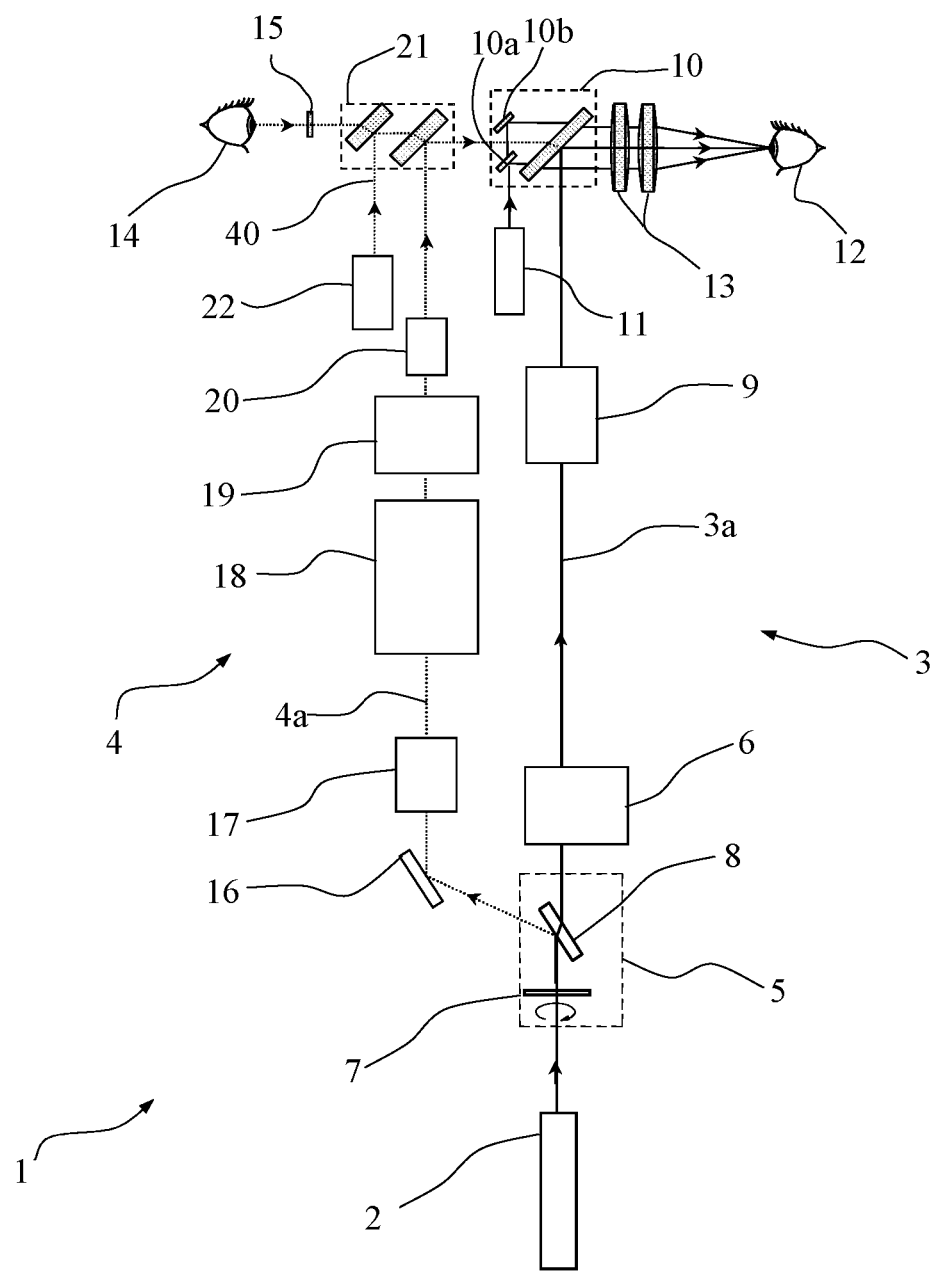
FIG. 1 is a schematic of an ophthalmic laser system including a photodisruptor for treatment of cataracts and an SLT optical system for treatment of glaucoma.

Embodiments of the present invention reside primarily in an ophthalmic laser system incorporating a reflex coaxial illuminator. Accordingly, the elements have been illustrated in concise schematic form in the drawings, showing only those specific details that are necessary for understanding the embodiments of the present invention, but so as not to obscure the disclosure with excessive detail that will be readily apparent to those of ordinary skill in the art having the benefit of the present description.

In this specification, adjectives such as first and second, left and right, and the like may be used solely to distinguish one element or action from another element or action without necessarily requiring or implying any actual such relationship or order. Words such as "comprises" or "includes" are intended to define a non-exclusive inclusion, such that a process, method, article, or apparatus that comprises a list of elements does not include only those elements but may include other elements not expressly listed, including elements that are inherent to such a process, method, article, or apparatus.

As described in PCT/AU03/01224, FIG. 1 shows an embodiment of an ophthalmic laser system 1 useful for treating glaucoma and secondary cataracts. The system is comprised of a laser module 2, a photodisruptor optical system 3 and SLT optical system 4.

A pulsed beam from the laser module 2 is attenuated at attenuator/beam steering module 5. An energy monitor system 6 measures the energy in each pulse. A half wave plate 7 within the attenuator/beam steering module 5 is adjusted to regulate the intensity of the pulsed beam in the photodisruptor optical system 3. A polarizing plate 8 may deflect the pulsed beam to the SLT optical system 4 depending on the orientation of the half wave plate 7.

Beam shaping optical module 9 expands the pulsed beam before it travels up to the folding mirror module 10. The expanded beam is then focused by objective lens 13 to produce an 8-10 μm beam waist at the treatment site which is required to produce photodisruption. An aiming laser module 11 provides a continuous, visible laser beam that is split into two beams and deflected by folding mirror module 10 to give a targeting reference for the treatment beam. These two aiming laser beams converge with the pulsed treatment beam at the target site in a patient's eye 12 via objective lens 13. An operator 14 views the patient's eye 12 through the folding mirror module 10. A safety filter 15 protects the eye of the operator. The folding mirrors 10a, 10b are positioned so that the viewing axis of the operator is not impeded.

The SLT optical system 4 comprises a mirror 16 that directs a deflected pulsed beam from the polarizing plate 8 in the attenuator/beam steering module 5 to the frequency doubling module 17. In one embodiment the frequency doubling module 17 converts the output of the laser module (such as Nd:YAG at 1064 nm) to twice the wavelength so that the output of the SLT optical system is in the visible spectrum. A suitable frequency doubling module 17 comprises a potassium titanyl phosphate (KTP) doubling crystal. The visible pulsed beam is effective in treating glaucoma in patients.

The pulsed visible beam may be attenuated at the SLT attenuator 18 to regulate the energy in the pulsed visible beam. An energy monitor system 19 measures the energy in each pulse.

A beam shaping module 20 adjusts the beam profile to provide an even energy distribution at the treatment plane. The visible beam then travels to a second folding mirror module 21. A second aiming laser module 22 provides a single aiming laser beam which is deflected by the second folding mirror module 21 and transmitted through folding mirror module 10 and objective lens 13. The continuous visible laser aiming beam generated by the second aiming laser module 22 coincides with the pulsed visible beam at the target site in a patient's eye 12 via objective lens 13.

Figure 2:
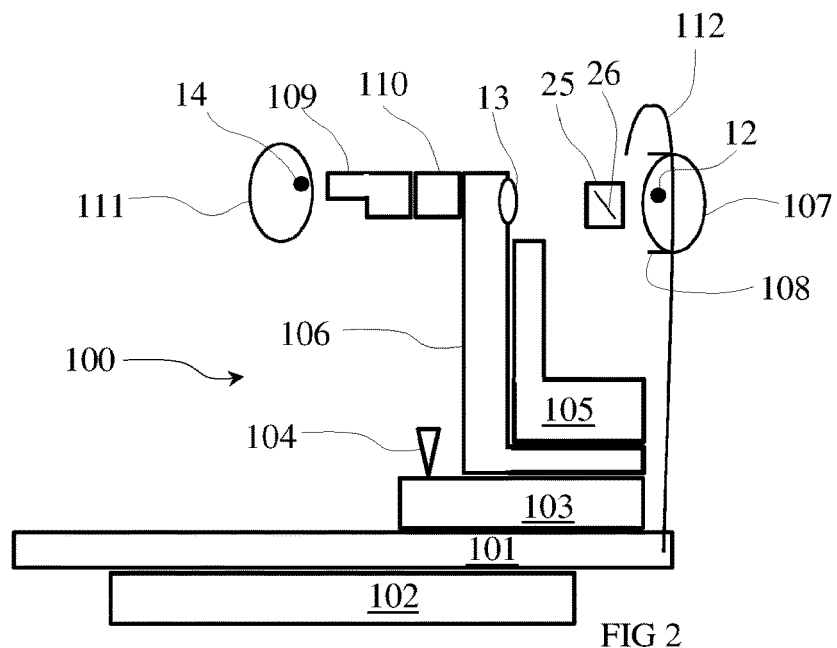
FIG. 2 is a schematic of the ophthalmic laser system of FIG. 1 embodied in a slit lamp assembly.

The ophthalmic laser system 1 is conveniently integrated into a slit lamp assembly 100, as shown in FIG. 2. The slit lamp assembly 100 consists of a table 101 with components of the system arranged in a console 102 located beneath the table 101. A slit lamp base 103 is movable on the table 101 using a joystick 104. The slit lamp 105 and the laser delivery head 106 are located on the slit lamp base 103 and move with it. The eye 12 of the patient 107 is fixed by the patient 107 resting on a chin rest 108 that is attached to the table 101. Binoculars 109 and magnification changer 110 are provided for viewing by the ophthalmologist 111.

The optical path for the ophthalmologist 111 is from the eye 14, through binoculars 109, magnification changer 110 and objective lens 13 to the eye 12 of the patient 107. The laser path is through the laser delivery head 106 and objective lens 13 to the eye 12. The aiming beam path is also through the laser delivery head 106 and objective lens 13 to the eye 12. A fixation lamp 112 provides illumination directly to the eye 12.

In order to provide illumination to the eye 12 coaxial with the laser treatment beams the arrangement shown in FIG. 1 is varied to include a reflex coaxial illuminator of the type described in International Patent Application number PCT/AU2013/000546. A reflex coaxial illuminator 25 comprises a reflex mirror 26 that directs light from the slit lamp 105 to the eye 12. As with the prior art, the light source 105 is suitably a broad spectrum (white) light source.

Figure 3:
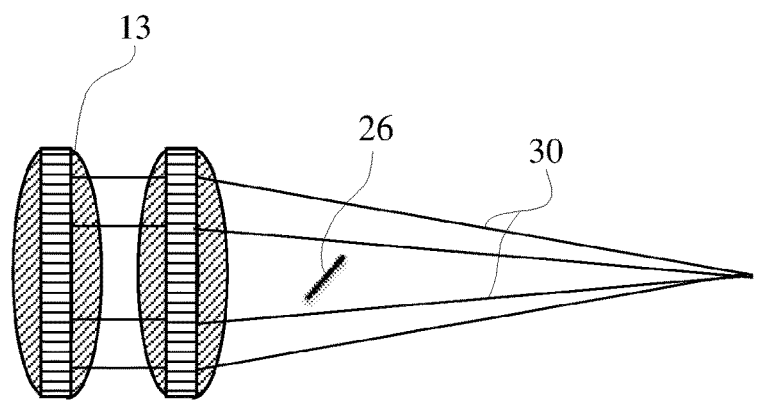
FIG. 3 shows the position of a reflex coaxial illuminator in the path of the photodisruptor.
Figure 4:
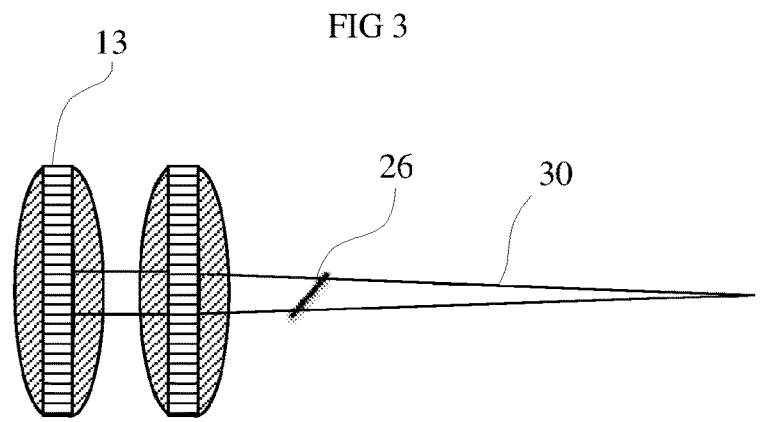
FIG. 4 shows the position of a reflex coaxial illuminator in the path of the SLT optical system.

As shown in FIG. 3, the mirror 26 is of a size and shape to be located between the pair of aiming beams 30 from the aiming laser 11 that are directed to the eye 12 by the objective lens 13. The user positions the aiming beams 30 by moving the slit lamp 105 to target a treatment zone while viewing the eye through binoculars 109. As shown in FIG. 4, the mirror 26 is in the path of the aiming beam 40 from the aiming laser 22.

Figure 5:
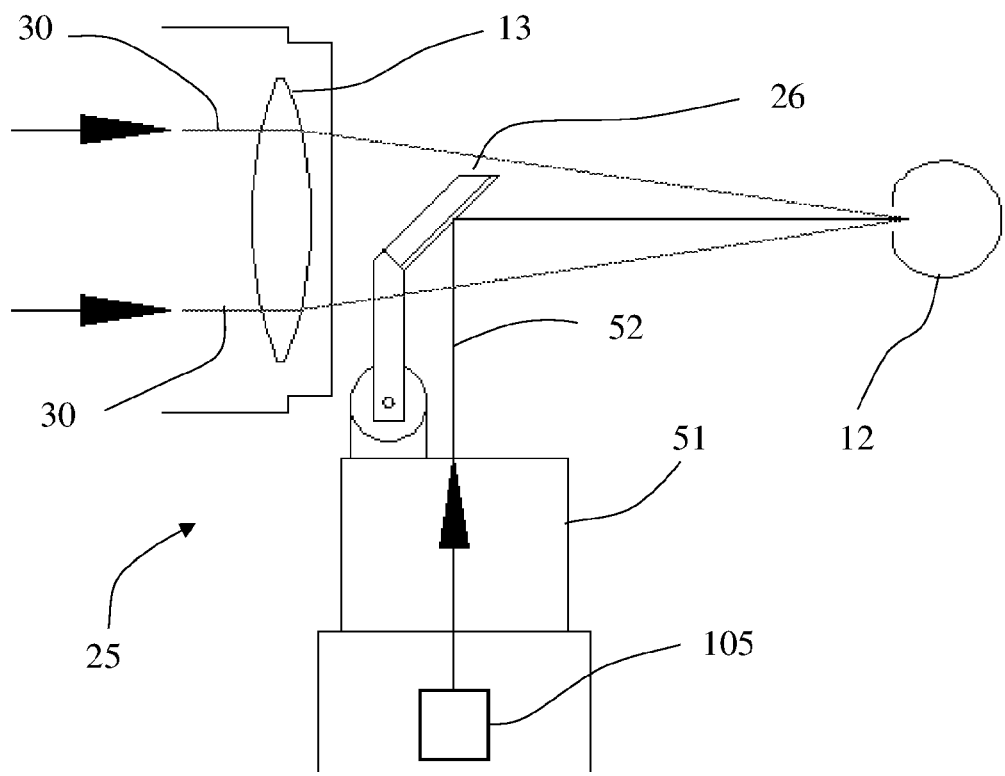
FIG. 5 shows the details of a reflex coaxial illuminator.

As described in International Patent Application number PCT/AU2013/000546 and shown in FIG. 5 the reflex coaxial illuminator 25 includes an actuator 51 to flip the mirror 26 out of the beam path when required but otherwise direct the slit lamp illumination 52 to the eye of the patient. However, for the laser system of FIG. 1 an additional solution is required since there are five separate beams that must be able to reach the eye while continuing to allow the physician to observe the treatment zone. The five beams are the slit lamp illumination 52, the photodisruptor aiming beams 30, the beam from the photodisruptor optical system 3, the SLT aiming beam 40, and the beam from the SLT optical system 4.

Furthermore, the ophthalmic laser described by reference to FIG. 1 may operate in either photodisruptor mode utilizing the laser beam along the beam path 3a shown in photodisruptor optical system 3 or in SLT mode utilizing the laser beam along the beam path 4a shown in SLT optical system 4.

In photodisruptor mode the requirements are:
Provide illumination the retina as close to co-axial as possible;
Allow the aiming beams to pass;
Allow the treatment beam to pass;
Not interfere with viewing by the user.
In SLT mode the requirements are:
Provide illumination to the anterior of the eye;
Allow the aiming beam to pass;
Allow the treatment beam to pass;
Not interfere with viewing by the user.

In order to meet all these requirements an interlock is provided to only permit operation of the SLT mode when the slit lamp assembly and reflex coaxial illuminator is completely moved out of the SLT beam path. When the slit lamp assembly is moved out of the SLT beam path it will also be out of the photodisruptor beam path and therefore both treatments will be enabled.

Figures 6, 7:
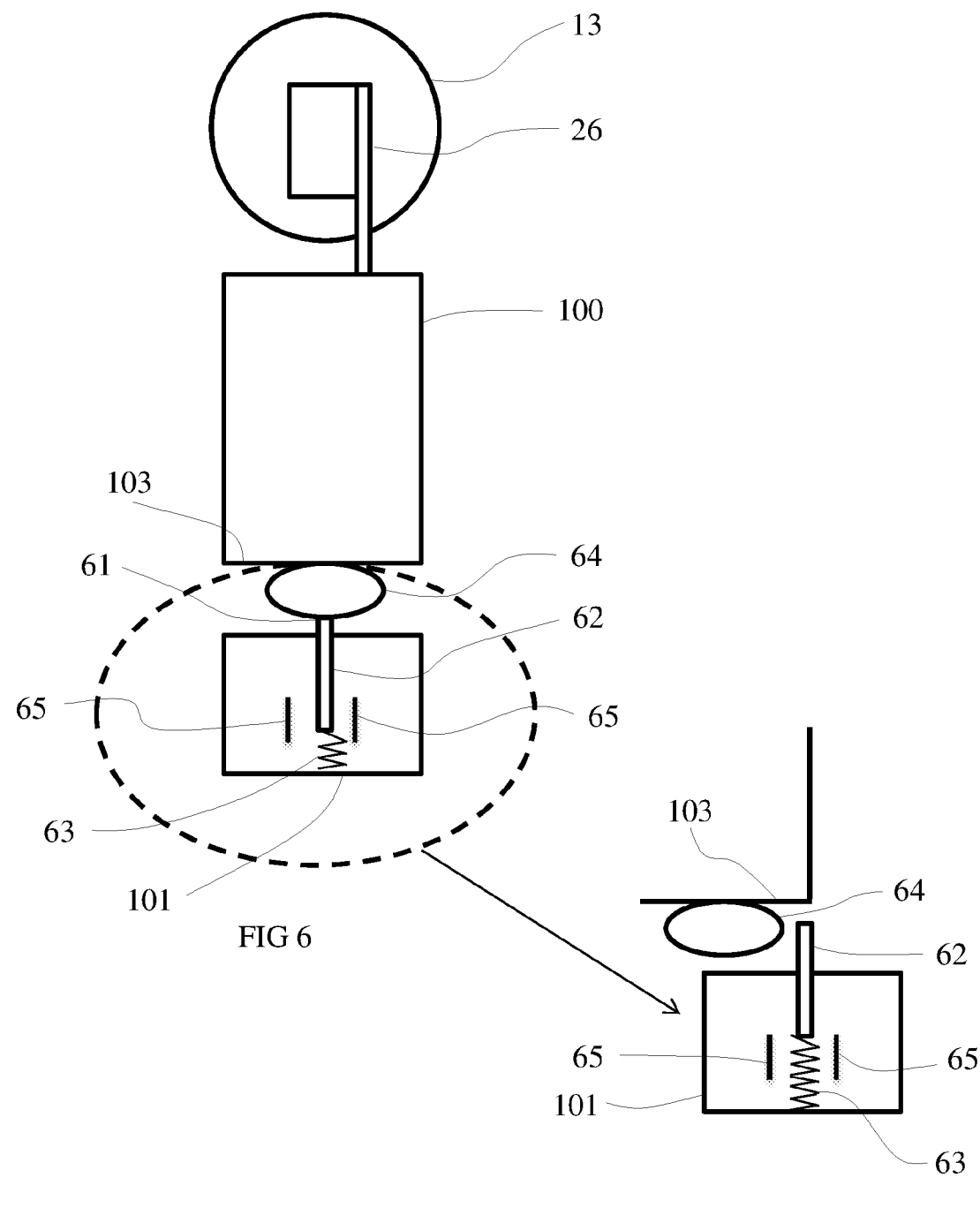
FIG. 6 shows a first embodiment of the invention in one position.
FIG. 7 shows the embodiment of FIG. 6 in another position.

When the slit lamp assembly and reflex coaxial illuminator are in the position depicted in FIG. 6 only the photodisruptor treatment using the first treatment beam path will be enabled. In this mode the reflex coaxial illuminator operates in the manner described above by flipping out of the path of the first treatment beam.

Referring to FIG. 6, there is shown a sketch of the slit lamp assembly 100 with reflex mirror 26 in the laser treatment path looking towards objective lens 13. A striker 61 is fitted to the bottom of the slit lamp assembly 100. The striker 61 comprises a pin 62 loaded by a spring 63 which is depressed by a protuberance 64 on the base of the slit lamp assembly base 103. When the slit lamp assembly is in a first position the protuberance 64 depresses the pin 62 which activates two optical sensors 65 mounted in the table 101 that provide a signal indicating that the slit lamp assembly 100, and hence the reflex coaxial illuminator 25 is in the SLT treatment beam path. In this position SLT treatment will not be available, but photodisruptor treatment will be available.

When the slit lamp assembly 100 with reflex 26 is moved away from the first position, as shown in FIG. 7, the spring 63 moves the pin 62 which is detected by the optical sensors 65. The optical sensors 65 provide a signal indicating that the slit lamp assembly 100, and hence the reflex coaxial illuminator 25 are out of the SLT treatment beam path. In this position SLT treatment and photodisruptor treatment will both be available.

FIG. 6 and FIG. 7 depict that the optical sensors 65 provide a signal when the slit lamp assembly is not in the first position and provide no signal when it is in the first position. Persons skilled in the art will appreciate that this can easily be reversed.

The signal from the optical sensors 65 is connected directly to the laser safety fire controller (not shown) and provides an on/off control.

Figure 8:
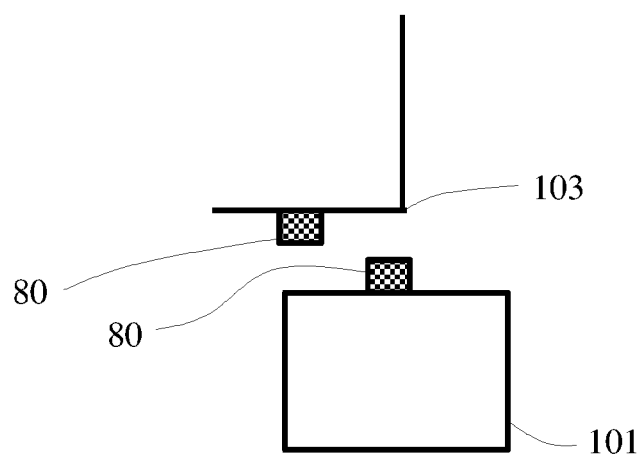
FIG. 8 shows a second embodiment of the invention.

The striker and optical sensor embodiment described with reference to FIG. 6 and FIG. 7 is only one example of an electronic safety interlock. Another example shown in FIG. 8 is to provide a direct electrical or optical interface between the slit lamp assembly base 103 and the table 101. When the slit lamp assembly 100 is in the first position the parts of the sensor 80 are aligned to provide a signal. When the slit lamp assembly 100 is moved away from the first position, as shown in FIG. 8, the parts of the sensor are not aligned so no signal is provided. The absence of a signal is configured to enable the SLT mode. This embodiment may be configured as an electrical interlock with contact electrodes positioned on the slit lamp assembly base 103 and the table 101 or an optical interlock with optical transmitter on the slit lamp assembly base 103 and optical receiver on the table 101, or vice versa.

From the above description it is clear that a primary application of the invention is in relation to an ophthalmic laser system for selective treatment of glaucoma and secondary cataract, although the invention may be applied to other ophthalmic laser systems that generate laser beams on two or more paths for different treatments. In the specific embodiment of treating glaucoma and secondary cataracts, the ophthalmic laser system comprises: a laser module in the form of a Q-switched laser which operates to produce pulsed radiation at a first wavelength; a first beam path adapted to treating secondary cataract incorporating an attenuator, beam shaping optics, and directing optics for directing the beam of short pulses at the first wavelength along a treatment beam path to an eye of a patient with secondary cataract; a second beam path adapted to treating glaucoma by selective laser trabeculoplasty incorporating a frequency conversion module that converts the pulsed beam at the first wavelength to a pulsed beam at a second wavelength, an attenuator, and directing optics for directing the pulsed beam at the second wavelength along the treatment beam path to an eye of a patient with glaucoma; beam steering optics for selectively deflecting the beam of short pulses at the first wavelength into the second beam path, the beam steering optics being operable between a first position in which the pulsed beam at the first wavelength is received by and follows the first beam path and a second position in which the pulsed beam at the first wavelength is deflected to, received by and follows the second beam path; a reflex coaxial illuminator comprising a reflex mirror movable on an axis from a position out of the treatment beam path to a position in the treatment beam path, wherein the reflex mirror directs illumination into an illumination path coaxial with the treatment beam path; and a safety interlock only allowing operation of the ophthalmic laser system on the first beam path if the reflex coaxial illuminator is in a first position and allowing operation of the ophthalmic laser system on either the first beam path or the second beam path if the reflex coaxial illuminator is not in the first position.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this invention is intended to embrace all alternatives, modifications and variations of the present invention that have been discussed herein, and other embodiments that fall within the spirit and scope of the above described invention.

The invention claimed is:

1. An ophthalmic laser system comprising:
a laser generator producing a beam of short pulses of radiation with high energy density at a first wavelength;
a first beam path incorporating optical elements for directing the beam at the first wavelength into a treatment beam path to an eye of a patient;
a second beam path incorporating a frequency doubling module that converts the beam at the first wavelength to a beam at a second wavelength, and optical elements for directing the beam at the second wavelength to the treatment beam path;
beam steering optics for selectively deflecting the beam at the first wavelength into the second beam path, the beam steering optics being operable between a first position in which the beam at the first wavelength follows the first beam path and a second position in which the beam at the first wavelength is deflected to the second beam path;
a reflex coaxial illuminator comprising a reflex mirror, wherein the reflex coaxial illuminator is movable on a first axis from a position in the treatment beam path to a position out of the treatment beam path, wherein the reflex mirror of the reflex coaxial illuminator is movable on a second axis out of the treatment beam path; and
a safety interlock only allowing operation of the ophthalmic laser system on the first beam path if the reflex coaxial illuminator is in a first position in the second beam path and allowing operation of the ophthalmic laser system on either the first beam path or the second beam path if the reflex coaxial illuminator is moved on the first axis out of the first position in the second beam path.

2. The ophthalmic laser system of claim 1 wherein the laser module is a flashlamp pumped, solid state laser.

3. The ophthalmic laser system of claim 1 wherein the laser module is a Nd:YAG laser producing the beam at the first wavelength at a wavelength of 1064 nm, and the beam at the second wavelength is frequency-doubled to 532 nm.

4. The ophthalmic laser system of claim 1 further comprising an aiming laser providing a targeting reference for said beam at said first wavelength.

5. The ophthalmic laser system of claim 1 further comprising an aiming laser providing a targeting reference for said beam at said second wavelength.

6. The ophthalmic laser system of claim 1 wherein the beam steering optics comprise a half wave plate and polarizer.

7. The ophthalmic laser system of claim 6 wherein the half wave plate is rotatably adjustable to regulate intensity.

8. The ophthalmic laser system of claim 1 wherein the frequency doubling module comprises a potassium titanyl phosphate (KTP) doubling crystal.

9. The ophthalmic laser system of claim 1 wherein the reflex mirror is rotated about the axis to move from the position in the treatment laser beam to the position out of the treatment laser beam.

10. The ophthalmic laser system of claim 1 wherein the reflex mirror is translated along the axis to move from the position in the treatment laser beam path to the position out of the treatment laser beam path.

11. The ophthalmic laser system of claim 1 wherein the reflex mirror is biased to maintain a position in the treatment laser beam path but is movable to a position out of the treatment laser beam path by an actuator.

12. The ophthalmic laser system of claim 11 wherein the reflex mirror is biased by a spring.

13. The ophthalmic laser system of claim 11 wherein the actuator is a motor or a solenoid or a piezoelectric device.

14. The ophthalmic laser system of claim 1 wherein the reflex mirror is moved from a position in the treatment laser beam path to the position out of the treatment laser beam path and back without noticeable interruption to viewing by a user.

15. The ophthalmic laser system of claim 1 wherein the safety interlock comprises a mechanical, electrical or optical interlock.

16. An ophthalmic laser system for selective treatment of glaucoma and secondary cataract, the ophthalmic laser system comprising:
a laser module comprising a Q-switched laser which operates to produce pulsed radiation at a first wavelength;
a first beam path adapted to treating secondary cataract incorporating an attenuator, beam shaping optics, and directing optics for directing a beam of short pulses at the first wavelength along a treatment beam path to an eye of a patient with secondary cataract;
a second beam path adapted to treating glaucoma by selective laser trabeculoplasty incorporating a frequency conversion module that converts a pulsed beam at the first wavelength to a pulsed beam at a second wavelength, an attenuator, and directing optics for directing the pulsed beam at the second wavelength along the treatment beam path to an eye of a patient with glaucoma;
beam steering optics for selectively deflecting the beam of short pulses at the first wavelength into the second beam path, the beam steering optics being operable between a first position in which the pulsed beam at the first wavelength is received by and follows the first beam path and a second position in which the pulsed beam at the first wavelength is deflected to, received by and follows the second beam path;
a reflex coaxial illuminator comprising a reflex mirror, wherein the reflex coaxial illuminator is movable on a first axis from a position out of the treatment beam path to a position in the treatment beam path, wherein the reflex mirror directs illumination into an illumination path coaxial with the treatment beam path, wherein the reflex mirror of the reflex coaxial illuminator is movable on a second axis out of the treatment beam path; and
a safety interlock only allowing operation of the ophthalmic laser system on the first beam path if the reflex coaxial illuminator is in a first position in the second beam path and allowing operation of the ophthalmic laser system on either the first beam path or the second beam path if the reflex coaxial illuminator is moved on the first axis out of the first position in the second beam path.

17. A method of treating secondary cataract or glaucoma in a patient using an ophthalmic laser system comprising:
a laser module producing a beam of short pulses of radiation with high energy density at a first wavelength;
a first beam path incorporating optical elements for directing the beam at the first wavelength into a treatment beam path to an eye of a patient;
a second beam path incorporating a frequency doubling module that converts the beam at the first wavelength to a beam at a second wavelength, and optical elements for directing the beam at the second wavelength to the treatment beam path;
beam steering optics for selectively deflecting the beam at the first wavelength into the second beam path, the beam steering optics being operable between a first position in which the beam at the first wavelength follows the first beam path and a second position in which the beam at the first wavelength is deflected to the second beam path;
a reflex coaxial illuminator comprising a reflex mirror, wherein the reflex coaxial illuminator is movable on a first axis from a position in the treatment beam path to a position out of the treatment beam path, wherein the reflex mirror of the reflex coaxial illuminator is movable on a second axis out of the treatment beam path; and
a safety interlock only allowing operation of the ophthalmic laser system on the first beam path if the reflex coaxial illuminator is in a first position in the second beam path and allowing operation of the ophthalmic laser system on either the first beam path or the second beam path if the reflex coaxial illuminator is moved on the first axis out of the first position in the second beam path; the method including the steps of:
operating the beam steering optics to select the first or second beam path depending on whether the patient has secondary cataract or glaucoma;
operating the safety interlock for either operation only on the first beam path or operation on either the first beam path or the second beam path; and
operating the laser system through the selected beam path to treat the patient.

* * * * *